United States Patent
Wixey

(10) Patent No.: US 10,591,032 B2
(45) Date of Patent: Mar. 17, 2020

(54) SPLIT NUT DRIVE

(71) Applicant: Intuitive Surgical Operations, Inc., Sunnyvale, CA (US)

(72) Inventor: Matthew A. Wixey, San Jose, CA (US)

(73) Assignee: Intuitive Surgical Operations, Inc., Sunnyvale, CA (US)

(*) Notice: Subject to any disclaimer, the term of this patent is extended or adjusted under 35 U.S.C. 154(b) by 230 days.

(21) Appl. No.: 15/699,441

(22) Filed: Sep. 8, 2017

(65) Prior Publication Data
US 2018/0073615 A1    Mar. 15, 2018

Related U.S. Application Data

(60) Provisional application No. 62/395,361, filed on Sep. 15, 2016.

(51) Int. Cl.
*F16H 25/20* (2006.01)
*A61B 34/30* (2016.01)
*A61B 34/00* (2016.01)
*A61B 17/072* (2006.01)
(Continued)

(52) U.S. Cl.
CPC ...... *F16H 25/2025* (2013.01); *A61B 17/07207* (2013.01); *A61B 34/30* (2016.02); *A61B 34/37* (2016.02); *A61B 34/74* (2016.02); *A61B 2017/00017* (2013.01); *A61B 2017/00477* (2013.01); *A61B 2034/302* (2016.02); *F16H 2025/2081* (2013.01)

(58) Field of Classification Search
CPC ............ F16H 25/2025; F16H 25/2021; F16H 25/2009; F16H 25/2006; Y10T 74/18696; Y10T 74/18704; F16D 1/08; F16D 7/00

USPC ............... 74/424.78, 89.38, 424.79
See application file for complete search history.

(56) References Cited

U.S. PATENT DOCUMENTS

| 4,207,898 A | 6/1980 | Becht |
| 5,382,885 A | 1/1995 | Salcudean et al. |
| 5,609,601 A | 3/1997 | Kolesa et al. |

(Continued)

FOREIGN PATENT DOCUMENTS

| WO | WO-2013084221 A1 | 6/2013 |
| WO | WO-2015153636 A1 | 10/2015 |
| WO | WO-2015175200 A1 | 11/2015 |

OTHER PUBLICATIONS

International Search Report and Written Opinion for Application No. PCT/US2017/050710, dated Dec. 14, 2017, 12 pages.

(Continued)

*Primary Examiner* — Jake Cook
*Assistant Examiner* — Gregory Robert Weber
(74) *Attorney, Agent, or Firm* — Schwegman Lundberg & Woessner, P.A.

(57) ABSTRACT

A medical device drive system including a lever body having portions defining a lever body cavity, a nut housing in the lever body cavity, and a first nut at least partially in the first nut cavity. The first nut is slideable in the first nut cavity between an engaged position in which the lead screw interface is engaged with the engagement portion of the lead screw, and a disengaged position in which the lead screw interface is not engaged with the engagement portion of the lead screw. The lead screw interface of the first nut is selectively engageable with the engagement portion of the lead screw by sliding the lever body and pin relative to the first nut housing.

19 Claims, 15 Drawing Sheets

(51) Int. Cl.
  *A61B 34/37*    (2016.01)
  *A61B 17/00*    (2006.01)

(56) References Cited

U.S. PATENT DOCUMENTS

| | | | |
|---|---|---|---|
| 6,770,081 B1 | 8/2004 | Cooper et al. | |
| 7,543,516 B2* | 6/2009 | Siefert | A61M 5/1456 |
| | | | 74/424.78 |
| 7,802,664 B2* | 9/2010 | Hanna | E05F 15/622 |
| | | | 188/265 |
| 7,984,663 B2 | 7/2011 | Dent | |
| 8,640,921 B2* | 2/2014 | Meron | A61B 17/00491 |
| | | | 222/137 |
| 8,644,988 B2 | 2/2014 | Prisco et al. | |
| 8,968,312 B2 | 3/2015 | Marczyk et al. | |
| 9,060,860 B2* | 6/2015 | Morris | A61F 2/2436 |
| 9,549,818 B2* | 1/2017 | Morrissey | A61F 2/2436 |
| 9,919,724 B2* | 3/2018 | Lubischer | B62D 1/181 |
| 2008/0245842 A1 | 10/2008 | Marczyk | |
| 2011/0060346 A1 | 3/2011 | Jensen et al. | |
| 2011/0118754 A1 | 5/2011 | Dachs, II et al. | |
| 2011/0208090 A1 | 8/2011 | Parihar | |
| 2013/0214029 A1 | 8/2013 | Scirica | |
| 2016/0100838 A1 | 4/2016 | Beaupré et al. | |
| 2016/0174984 A1 | 6/2016 | Smith et al. | |
| 2016/0220369 A1* | 8/2016 | Chalekian | A61F 2/2436 |
| 2018/0274601 A1* | 9/2018 | Saito | F16D 23/12 |

OTHER PUBLICATIONS

International Search Report and Written Opinion for Application No. PCT/US2017/050731, dated Dec. 15, 2017, 14 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

U.S. Appl. No. 16/333,924, filed Mar. 15, 2019, Medical Device Drive System.

U.S. Appl. No. 16/333,926, filed Mar. 15, 2019, Medical Device Drive System.

* cited by examiner

SPLIT NUT DRIVE

CLAIM OF PRIORITY

This application claims the benefit of priority under 35 U.S.C. § 119(e) to U.S. Provisional Patent Application Ser. No. 62/395,361, filed on Sep. 15, 2016, which is incorporated by reference herein in its entirety.

BACKGROUND

Medical device systems can include components that are driven by drive mechanisms such as electric motors. Drive components such as gears, levers, and tubes can be used to translate movement through a drive system to a medical tool. For example, surgical systems can include tools that are controlled and driven by mechanical drive systems. Surgical systems can include tools such as cutters, staplers, and cautery tools.

SUMMARY

An example medical device drive system can include a lever body having portions defining a lever body cavity, and a lead screw extending through the lever body cavity. The lead screw can have proximal end, a distal end, and an engagement portion between the proximal end and the distal end. The proximal end and distal end can define a lead screw axis extending from the proximal end to the distal end of the lead screw. The example medical device drive system can further include a first nut housing having a first nut cavity. The first nut housing can be at least partially in the lever body cavity, and can be slidable in the lever body cavity. The medical device drive system can further include a first nut at least partially in the first nut cavity. The first nut can have a first slot, and a lead screw interface sized and shaped to engage with the engagement portion of the lead screw. The first nut can be slidable in the first nut cavity between an engaged position in which the lead screw interface is engaged with the engagement portion of the lead screw, and a disengaged position in which the lead screw interface is not engaged with the engagement portion of the lead screw. The example medical device drive system can further include a pin coupled to the lever body. The pin can be slidable in the first slot of the first nut. The lead screw interface of the first nut can be selectively engaged with the engagement portion of the lead screw by sliding the lever body and pin relative to the first nut housing.

In some examples, the medical device drive system can have a first state and a second state. In the first state, the pin can be in a first pin position in the first slot, the first nut housing can be in a first nut housing position relative to the lever body, and the lead screw interface of the first nut can be engaged with the lead screw engagement portion to prevent movement of the lead screw along the lead screw axis. In the second state, the pin can be in a second pin position in the first slot, the first nut housing can be in a second nut housing position relative to the lever body, and the lead screw interface of the first nut is not engaged with the lead screw engagement portion. The pin can be slidable in the first slot from the first pin position to the second pin position as the first nut housing is moved from the first nut housing position to the second nut housing position.

In some examples, the medical device drive system can include a spring in the lever body cavity. The spring can be sized and shaped to exert a drive gear turns biasing force on the first nut housing and the lever body. The biasing force can bias the pin toward the first pin position in the first slot of the first nut. In some examples, when the pin is removed, the springs can bias the nut into the engaged position, so that the nut is nominally engaged with the lead screw. In some examples, the split nature of the nut can allow disengagement of the nut from the screw to enable manual retraction of a drive member, such as a drive tube, without turning the screw.

In some examples, the medical device drive system can include a second nut housing having a second nut cavity, and a second nut having a second slot and a second lead screw interface sized and shaped to engage with the engagement portion of the lead screw. The second nut can be at least partially in the second nut cavity and can be slidable in the second nut cavity. In some examples, the first nut can be partially in the first nut cavity and partially in the second nut cavity, and the second nut can be partially in the first nut cavity and the second nut cavity.

The medical device drive system can also include a second pin coupled to the lever body. The second pin can be slidable in the second slot of the second nut. In some examples, the first nut can further include a third slot, and the second nut can further include a fourth slot, and the medical device drive system can further include a third pin coupled to the lever body, the third pin can be slidable in the third slot, and a fourth pin coupled to the lever body, the fourth pin can be slidable in the fourth slot. In some examples, the first slot can define a first pin path, the second slot can define a second pin path, the third slot can define a third pin path, and the fourth slot can define a fourth pin path. In some examples, the third pin path can be parallel to the first pin path, and the fourth pin path can be parallel to the second pin path In some examples of the medical device drive system the first nut can be slidable along a first axis, and the first nut sliding axis and the lead screw axis can define a first angle. The second nut can be slidable along a second nut sliding axis, and the second nut sliding axis and the lead screw axis define a second angle. The magnitude of the second angle can be the same as the magnitude of the first angle. In some examples, the first nut sliding axis and second nut sliding axis can be perpendicular to the lead screw axis.

In some examples, the medical device drive system can be configured such that when the lever body is biased in a first direction along the lead screw axis, the first nut and second nut are biased away from the lead screw by the respective first pin and second pin, and, when the lever body is biased in a second direction along the lead screw axis, the first nut and second nut are biased toward the lead screw by the respective first pin and second pin.

In some examples, the medical device drive system can further include a chassis. The lead screw can be rotatably coupled to the chassis, and the lever body can be slidably coupled to the chassis. The medical device drive system can further include a drive gear coupled to the lead screw and the chassis. When the lead screw interface on the first nut is engaged with the lead screw engagement portion, rotation of the drive gear can turn the lead screw and drive the first nut and first nut housing along the lead screw axis. In some examples, the medical device drive system can further include a member, such as a drive tube, that is coupled to the first nut housing. The drive tube can, for example, be connected to the nut housing. The drive tube can have a proximal end, and distal end, and a drive tube axis defined by the proximal end and the distal end. Rotation of the drive gear can turn the lead screw and drive the drive tube along the drive tube axis.

In some examples, the medical device drive system can further include a surgical instrument coupled to the drive member and the lead screw. In an example, rotation of the lead screw can cause a first manipulation of the surgical instrument, and driving the drive member along the drive member axis can cause a second manipulation of the surgical instrument.

An example medical device can include a lead screw can have a proximal end, a distal end, and a lead screw engagement portion between the proximal end and the distal end. The proximal end and distal end can define a lead screw axis extending from the proximal end to the distal end. The medical device can further include a lever body, a first nut slidably coupled to the lever body, and a second nut slidably coupled to the lever body. The first nut can have a first nut engagement portion sized and shaped to engage with the lead screw engagement portion, and the second nut can have a second nut engagement portion sized and shaped to engage with the lead screw engagement portion. The first nut and second nut can be slidable toward and away from the lead screw axis. The medical device can further include one or more drive portions coupled to the lever body. The one or more drive portions can have one or more drive surfaces in contact with the first nut and the second nut. The one or more drive surfaces can be oblique to the lead screw axis, wherein displacement of the lever body along the lead screw axis in a first direction biases the first nut and second nut toward the lead screw axis, and displacement of the lever body along the lead screw axis in a second direction biases the first nut and second nut away from the lead screw axis. In an example device, the first nut includes a first slot, the second nut includes a second slot, and the one or more drive portions include one or more pins extending into the first slot and second slot.

In some examples, the lever body can include portions defining a lever body cavity having a proximal end, a distal end, and a lever body axis defined between the proximal end and the distal end. The medical device can further include one or more nut housings having one or more nut body cavities. The one or more nut housings can be at least partially in the lever body cavity and can be slidable in the lever body cavity along the lever body axis. The first nut and second nut each can be at least partially in the one or more nut body cavities and can be slidable in the one or more nut body cavities.

In some examples, the one or more nut housings include a first nut housing can have portions defining a first nut cavity, and a second nut housing can have portions defining a second nut cavity. The first nut can be at least partially in the first nut cavity, and can be slidable in the first nut cavity toward and away from the lead screw axis. The second nut can be at least partially in the second nut cavity, and can be slidable in the second nut cavity toward and away from the lead screw axis.

In some examples, the medical device can further include a drive member such as a drive tube coupled to the one or more nut housings, an instrument coupled to a distal end of the drive tube, and a drive system coupled to the lead screw and configured to turn the lead screw. When the first nut engagement portion is engaged with the lead screw engagement portion, turning the lead screw drives the first nut, the second nut, the first nut housing, the second nut housing, the drive tube, and the instrument axially along the lead screw axis.

An example selectively engageable medical device drive assembly can include a lever body having a proximal end, a distal end, and portions defining an interior cavity, and a nut housing in the interior cavity of the lever body. The nut housing can be slidable relative to the lever body. The nut housing can have a proximal opening, a distal opening, portions defining a nut cavity, and portions defining a first nut housing slot and a second nut housing slot. The a lead screw can have a proximal end, a distal end, and a lead screw body extending from the proximal end to the distal end, the lead screw body defining a lead screw axis, the lead screw body extending through the proximal opening and distal opening in the nut housing, and an engagement portion of the lead screw can be at least partially in the interior cavity of the nut housing. The medical device drive assembly can further include a split nut in the nut cavity, the split nut including a first nut part and a second nut part, the first nut part including a first engagement portion and a first slot, and the second nut part including a second engagement portion and a second nut slot. The first engagement portion and second engagement portion can be sized and shaped to engage with the lead screw engagement portion. The medical device drive assembly can further include a first pin in the first nut slot and first nut housing slot, and a second pin in the second nut slot and the second nut housing slot. In some examples, the nut housing can include a first nut housing part and second nut housing part, the first nut housing part and second nut housing part each can have mating surfaces, the first nut housing part and second nut housing part together defining the nut cavity.

In some examples, sliding the nut housing relative to the lever body moves the first pin in the first nut slot and first nut housing slot, and moves the second pin in the second nut slot and second nut housing slot, the first pin and second pin biasing the respective first engagement portion of the first nut and the second engagement portion of the second nut out of engagement with the engagement portion of the lead screw.

Each of these non-limiting examples can stand on its own, or can be combined in various permutations or combinations with one or more of the other examples.

This Summary is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Medical device drive systems can be used to control an instrument that is coupled to a drive system with a shaft. A teleoperated surgical system, for example, can employ a medical device drive system to control a surgical instrument that can be inserted into a patient to perform a surgical procedure.

An example medical device drive system can include a lead screw and a nut that can be selectively engaged with the lead screw. Engagement of the nut can couple the lead screw to other components of a drive system. Disengagement of the nut can allow for movements of portions of the drive system without turning the lead screw.

In some examples, the nut can include a split nut, i.e. a nut component that is divided into two more pieces that can slide into and out of engagement with the lead screw. In some examples, by sliding the pieces away from the lead screw, the drive system can be disengaged from the lead screw, which can enable manual retraction of portions of the drive system without turning the lead screw. This can be important, for example, during robot-assisted surgery, to allow manual retraction of a surgical tool without use of a computerized control system.

In some examples, engagement and disengagement of a split nut can be accomplished with pins that extend through portions of the split nut. The split nut can be configured with slots that are sized and shaped so that movement of the pins biases portions of the split nut toward each other, or away from each other, depending on the direction of movement of the pins. In some examples, an apparatus can include an additional structure, such as a nut housing, that has slots that are sized and shaped to receive the pins, but are oblique to the slots in the split nut, so that movement of the additional structure the pins can bias the pins in a direction that causes the split nut to engage with, or disengage from, a lead screw or other drive component.

Figure 1A:
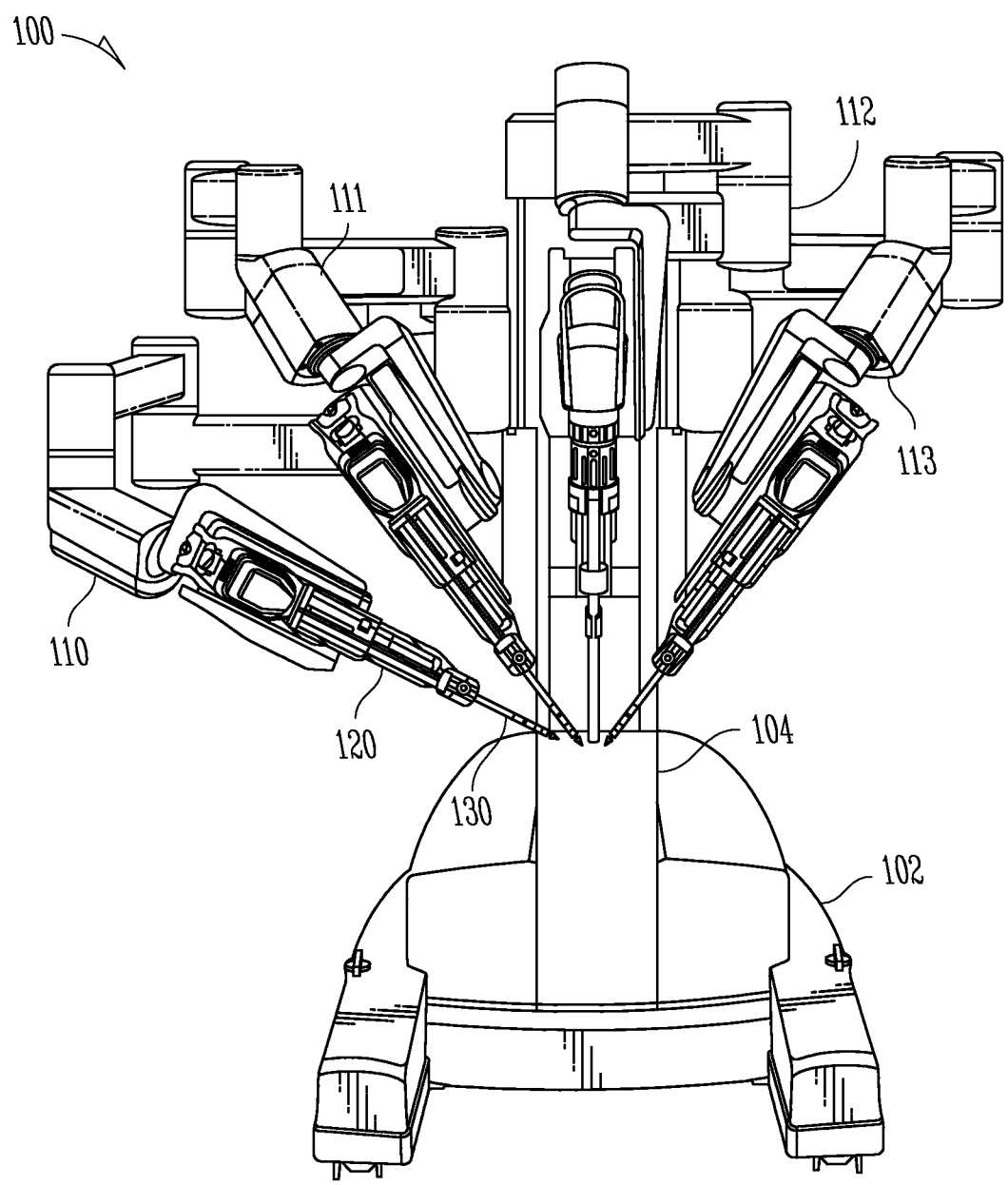
FIG. 1A is an illustration of an example instrument system for use in robot-assisted minimally invasive surgery.
Figure 1B:
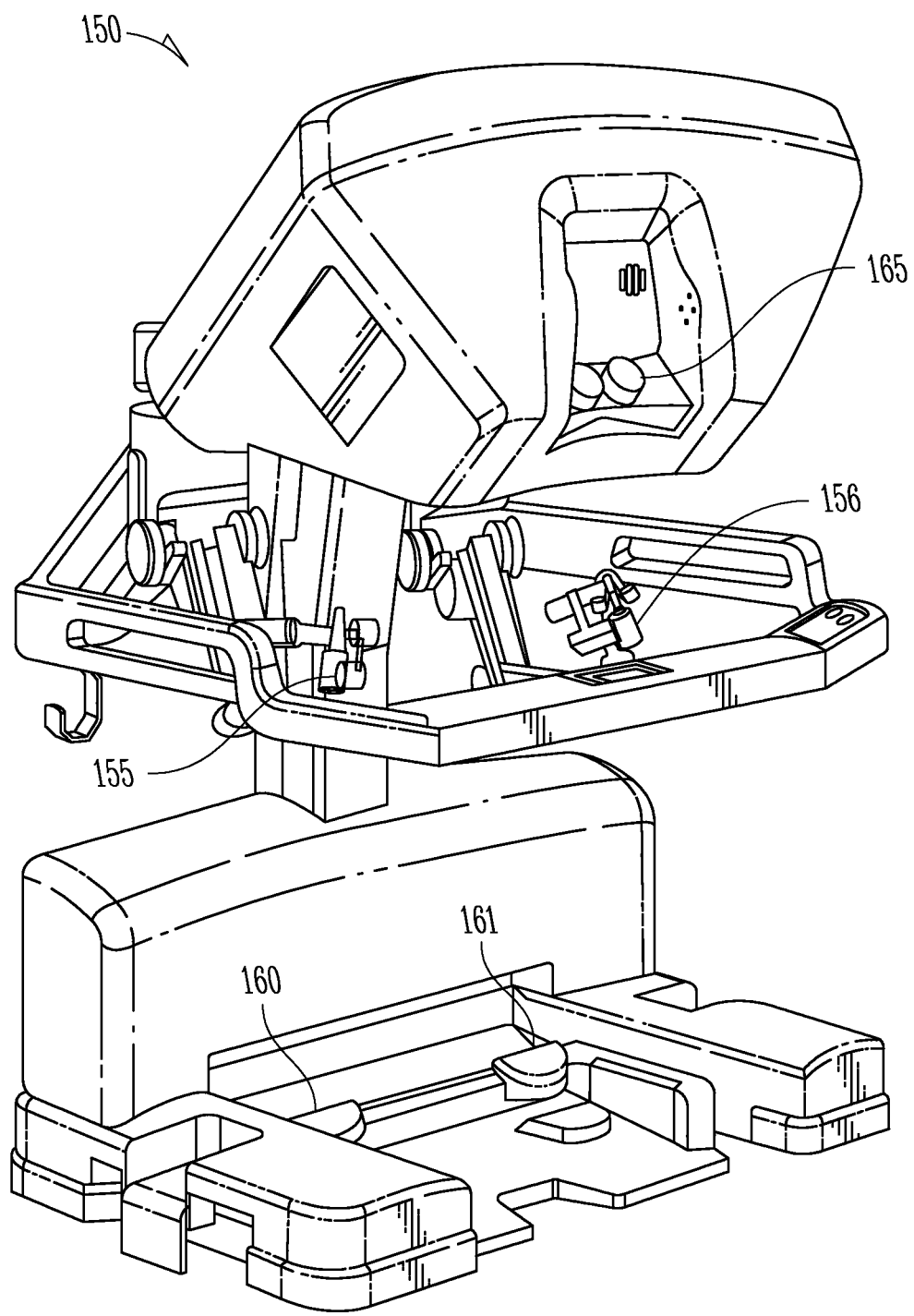
FIG. 1B is an illustration of an example physician console for use in robot-assisted minimally invasive surgery.
Figure 1C:
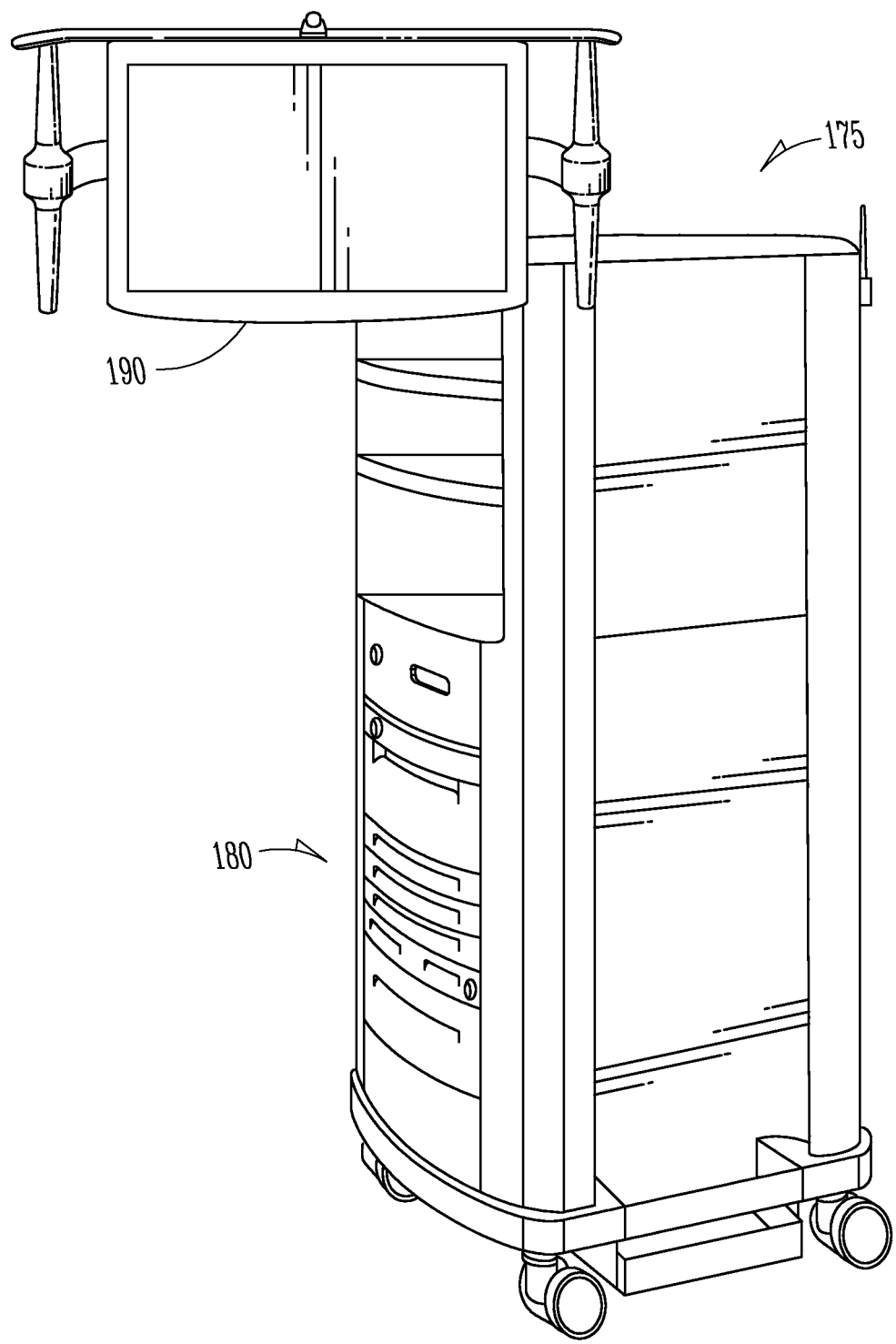
FIG. 1C is an illustration of an example control cart for use in robot-assisted minimally invasive surgery.

FIGS. 1A, 1B, and 1C illustrate an example robot-assisted minimally invasive surgical system. FIG. 1A shows an instrument system 100 (sometimes known as a "patient side cart") that can be situated near a patient operating table (not shown). FIG. 1B shows a surgeon console 150 that can include controls and a viewing system. FIG. 1C shows a control cart 175 that can include, for example, processing equipment and communication equipment.

Referring again to FIG. 1A, the system 100 can include a base 102, a support tower 104, and one or more manipulator arms 110, 111, 112, 113, which can be mounted on the support tower. Alternatively, the manipulator arms 110, 111, 112, 113 can be connected to a main boom (not shown), which can be movable. An instrument 130 can be mounted to an instrument mount 120 on one of the manipulator arms. A cannula (not shown in FIG. 1A) can be mounted to a cannula mount. An instrument 130 can be inserted through a cannula seal in the cannula, and into the patient (not shown) for use in a surgical or other medical procedure. Through movement of the manipulator arms, the orientation of the instrument can be controlled in multiple dimensions, e.g. lateral, horizontal, vertical, angular movements in one, two, or three planes.

FIG. 1B shows an example physician console 150. The physician console can include hand control 155, 156 and pedal controls 160, 161. The hand controls 155, 156, and pedal controls 160, 161 can be used to control equipment at the patient side cart. For example, portions of a distal end of an instrument can be manipulated using instrument controls. The controls can include haptic feedback features so that a physician can interpret physical information, such as resistance or vibration, through the controls. The physician console 150 can also include a viewing system 165 that can display video or other images of a surgical site.

FIG. 1C shows an example control cart 175. The control cart can include processing equipment 180 for processing controls, facilitating communication between the physician console and the patient side cart, or a remote site. The control cart 175 can also include a display 190, which can show images that the physician is seeing on the physician console, a video feed from a camera in the patient, or other information. In an example configuration, signals input at a surgeon console 150 can be transmitted to the equipment 180 on the control cart, which can interpret the inputs and generate commands that are transmitted to the patient side cart 100 to cause manipulation of an instrument 130 or portions of a manipulator arm 110. The equipment 180 is shown on a cart for exemplary purposes, but could also be arranged in various configurations, e.g., it could be integrated as part of the physician console, the patient side cart, or both, or divided between the physician console and patient side cart. The equipment can also be provided as software, hardware, or both, on an installed or remote system.

Figure 1D:
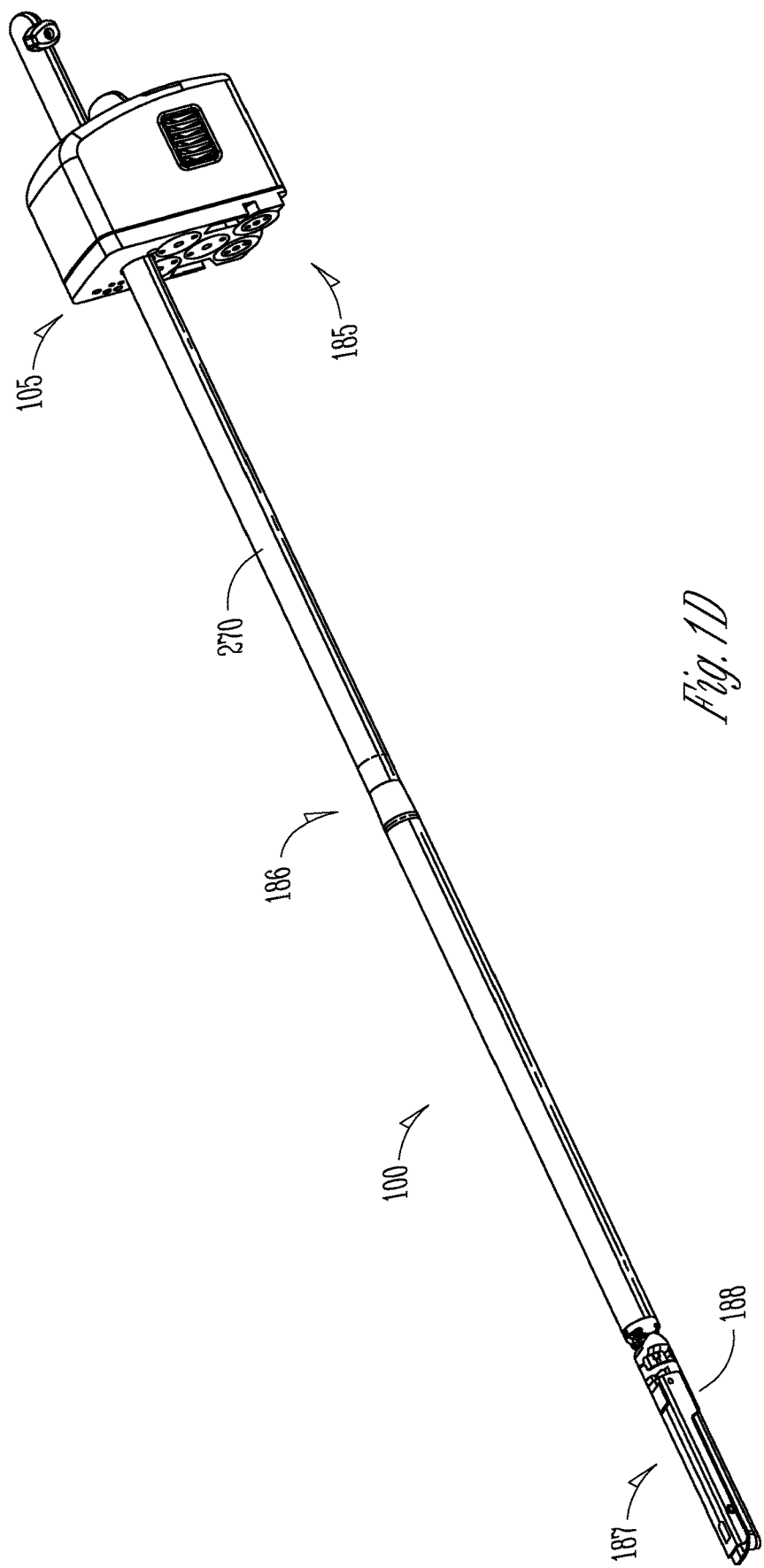
FIG. 1D is a perspective view of an example medical device drive system connected to an example medical tool.

FIG. 1D shows an example medical device system 101 that can be mounted on and used with the instrument system 100 shown in FIG. 1A. The medical device system 101 can include a proximal portion 105 including an interface 185 that can couple to a computerized control system such as the system illustrated in FIGS. 1A, 1B, and 1C, a middle portion 186 that can include drive components such as a drive member (not shown in FIG. 1D), and a distal portion 187 that can include an surgical tool 188. The surgical tool 188 can, for example, be any of a variety of surgical tools, such as a cutter, grasper, a cautery tool, a camera, a light, or a surgical stapler. The surgical tool 188 can be the instrument 130 shown in FIG. 1A. For the purpose of this document, the terms "tool" and "instrument" are interchangeable.

Figure 2A:
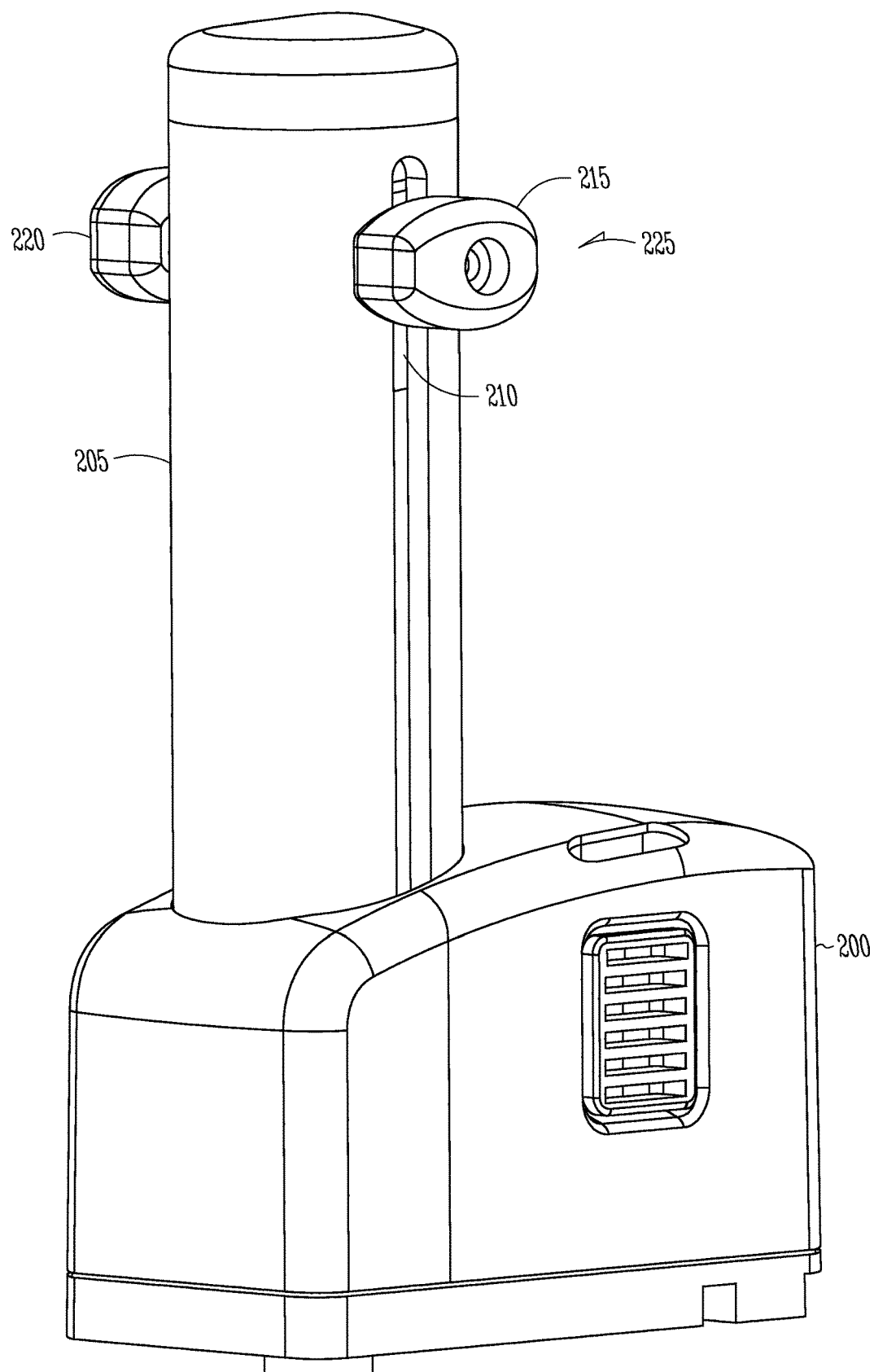
FIG. 2A is a perspective view of a proximal end of the medical drive system of FIG. 1D.

FIG. 2A shows the proximal portion 105 of the medical device system 101, which can include a main housing 200 and a housing extension 205 coupled to the main housing. The housing extension 205 can include housing extension slots 230 to allow a lever assembly 225 to travel up and down in the housing extension 205. The lever assembly 225 can include a lever body (shown in FIG. 3A) that can be coupled to handles 215, 220.

Figure 2B:
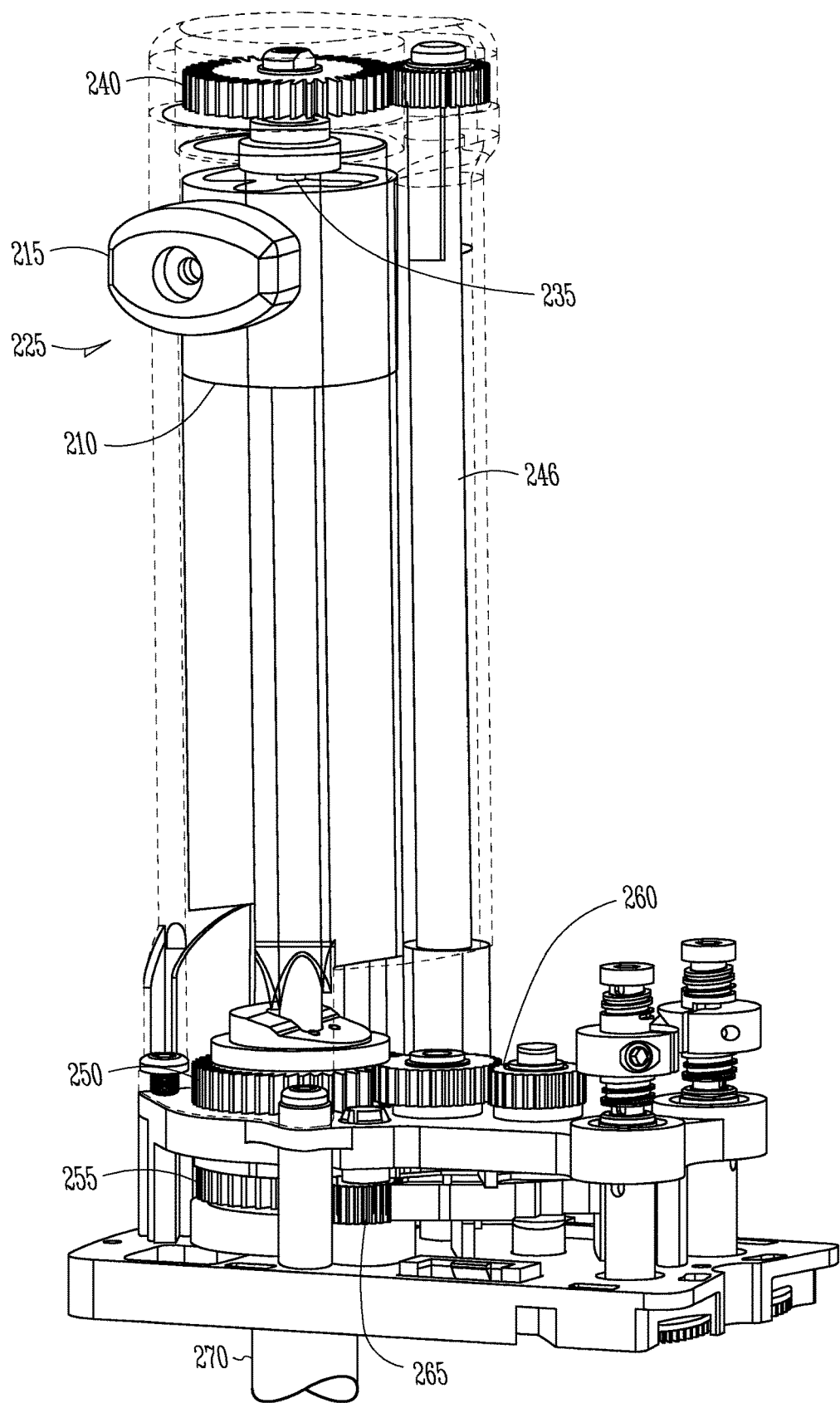
FIG. 2B is a partially cut-away perspective view of the medical device drive system of FIG. 1D.

FIG. 2B is a perspective view of the proximal portion 105 of shown in FIG. 2A that has the housing 200 and housing extension 205 removed to show internal components. The view in FIG. 2B is rotated about 90 degrees to show components that would otherwise be hidden. A lead screw 235 can extend through the lever body 210. The drive system can also include a drive gear 240 that is coupled to the lead screw 235, and a drive input gear 245 that is engaged with the drive gear 240. The drive input gear 245 can be connected to a drive input 246 that is coupled with a portion of the drive interface (not shown in FIG. 2B) to allow for control of the drive input gear 245 by a computerized control system, such as a telerobotic surgical system. The telerobotic surgical system can, for example, be the da Vinci® surgical system available from Intuitive Surgical®. In an example, the lead screw 235 can be configured to prevent axial movement of the lead screw 235, for example by connecting the lead screw 235 to the drive gear 240. In an example, the lead screw 235 can be coupled to a drive member (not shown), such as a drive tube, that is allowed to move axially, but prevented from rotating, so that rotation of the lead screw causes axial movement of the drive member. The drive member can be coupled to the surgical tool 120 so that axial movement of the drive member causes an operation or movement (e.g. advancement) of the tool. Second and third drive gears 250, 255 can be coupled to respective second and third input gears 260, 265, which can coupled to additional portions of the drive interface to allow for control of other operations of the medical tool, such as rotation, steering, and the like. In an example, rotation of input gear 265 causes rotation of drive gear 255, which causes drive shaft 270 to rotate, which can, for example, cause the surgical tool 120 to rotate.

As will be described in further detail in reference to FIGS. 3A-3G, the medical device system 101 can be configured so that proximal movement of the handles 215, 220 and lever body disengages a split nut (shown in FIG. 3F) from the lead screw 235, which can allow a user to manually retract the lever body and connected components, such as a drive member and surgical instrument.

Figure 3A:
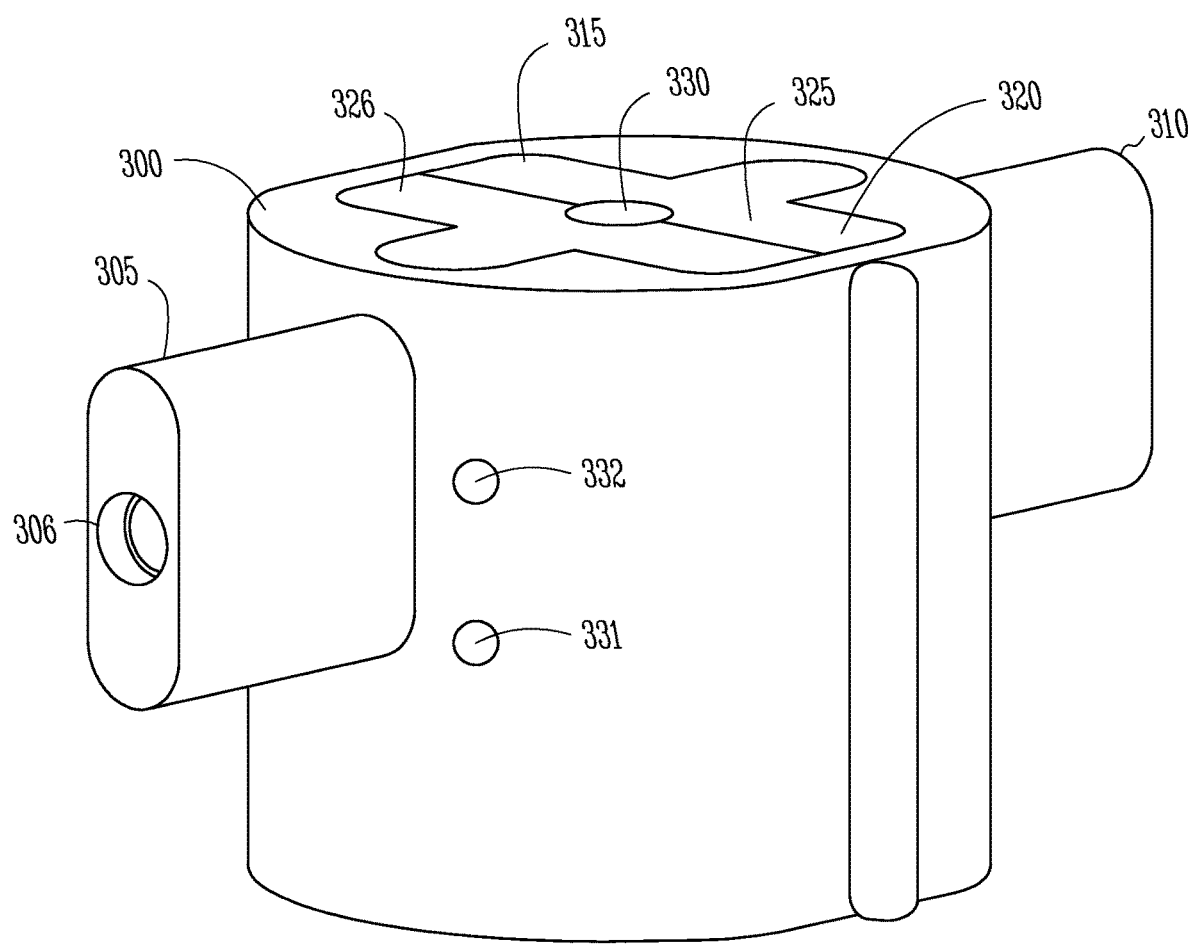
FIG. 3A is a perspective view of an example lever body that can be used in the medical device drive system of FIG. 1D, with example nut housing portions assembled into the lever body.
Figure 3B:
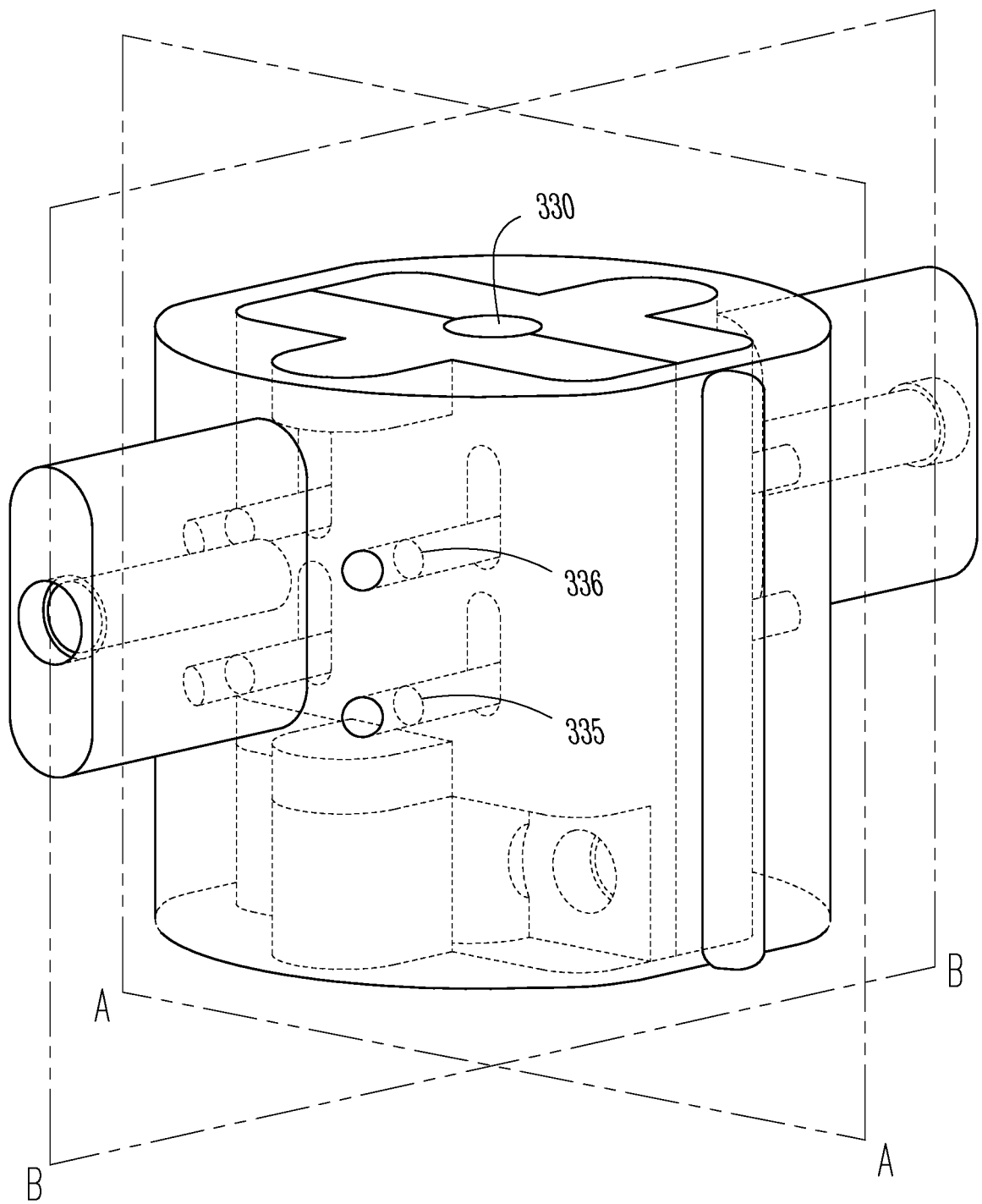
FIG. 3B is a partially cut-away perspective view of the lever body and nut housing portions of FIG. 3A, with pins extending through slots in the nut housing.
Figure 3C:
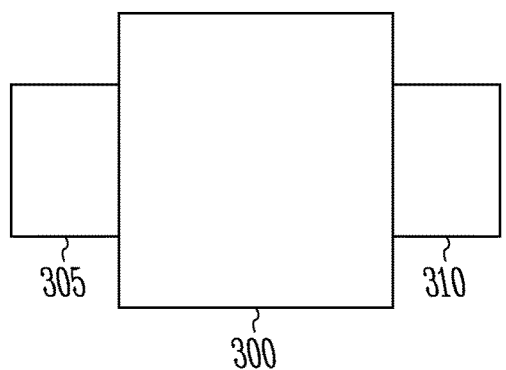
FIG. 3C is a side view of an example lever body such as the lever shown in FIG. 3B.
Figure 3D:
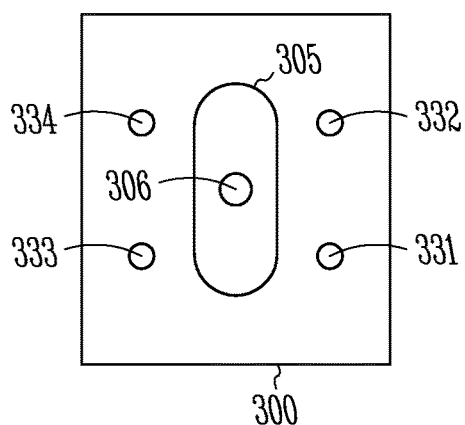
FIG. 3D is a front view of the example lever body shown in FIG. 3C.
Figure 3E:
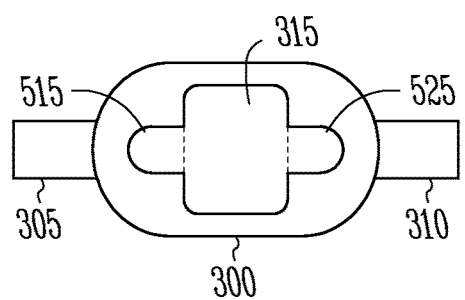
FIG. 3E is a bottom view of the example lever body shown in FIG. 3C.

FIG. 3A is a perspective view of the lever assembly 225 that shows lever body 210 and some internal components. FIG. 3B is a perspective view of the lever assembly 225 at the same angle, with portions of the lever body 210 cut away to show components assembled inside the lever body. Front, side, and top views of the lever body 210 are provided in FIGS. 3C, 3D, and 3E.

Lever body 210 can include a main body 300 and lever portions 305, 310 extending from the main body. The lever portions 305, 310 can be sized and shaped to extend through the housing extension slots 230. Each lever portion 305, 310 can include a hole 306, 311 for receiving a connecting member (not shown) such as a screw or press-fit pin to connect the handles 215, 220 (shown in FIGS. 2A and 2B).

The main body 300 can include portions defining an interior cavity 315 that is sized and shaped to receive a nut housing 320 that can be formed from nut housing portions 325, 326. The nut housing portions 325, 326 can define a passage 330 that is sized and shaped to accommodate a lead screw 235 (shown in FIG. 4) that can extend through the lever body 210 and nut housing portions 320, 325. While nut housing 320 is shown formed from two nut housing portions 325, 326, configurations that include a single nut housing portion, or more than two nut housing portions are also possible.

The main body 300 can also include portions defining one or more holes 331, 332, 333, 334 that are sized and shaped to receive a drive member such as a pin. While the example illustrated holes and pins are shown as round (i.e. circumferential cross-section), the pins can be other shapes, such as (in cross-section) square, rectangular, other polygons, elliptical, or other shapes.

Figure 3F:
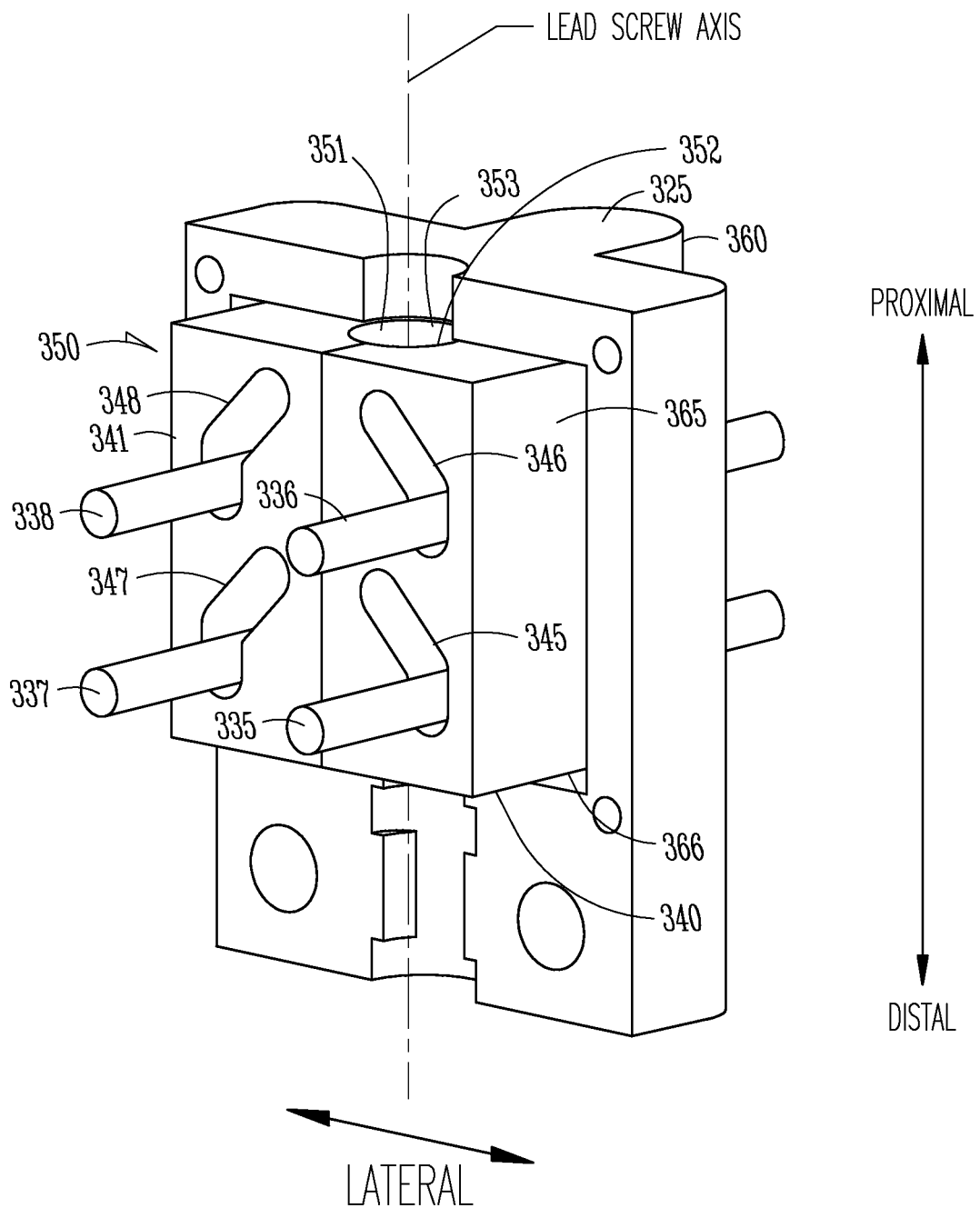
FIG. 3F shows a split nut in half of nut housing portion.
Figure 3G:
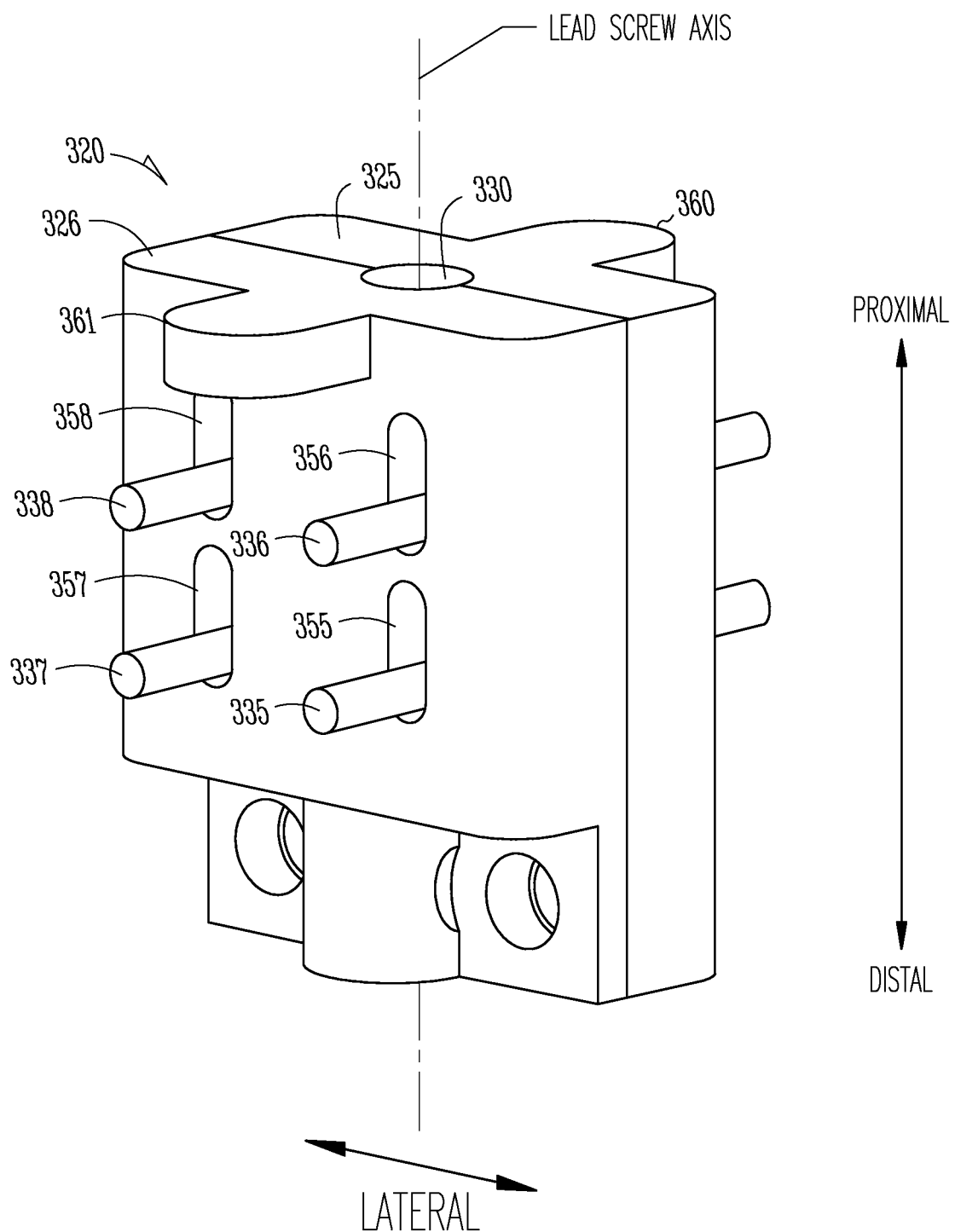
FIG. 3G shows two nut housing portions assembled to form a nut housing that can house a split nut.

FIG. 3F shows a split nut 350 in nut housing portion 325. As shown in FIG. 3G, nut housing portion 326 can be assembled with nut housing portion 325 to form nut housing 320 that can at least partially house the split nut 350. The nut housing portion 325 and nut housing portion 326 can be sized and shaped to allow the nut portions 340, 341 to slide laterally relative to the nut housing portions 325, 326. While the split nut 350 is shown fully enclosed in the nut housing, other configurations are possible where the split nut is just partially inside the nut housing. As will be described in further detail, the nut portions 340, 341 and nut housing portions 325, 326 can be configured with slots that are sized and shaped to accommodate drive members or drive portions, such as pins that extend through one of the nut portions 340, 341 and the nut housing portions 325, 326. The slots can be configured so that movement of the pins relative to the nut housing 320 in a first direction relative to the nut housing causes the nut portions 340, 341 to slide away from each other to disengage from a lead screw (shown in FIG. 4B). Movement of the pins in a second, opposite direction relative to the nut housing 320 causes the nut portions 340, 341 to slide toward each other to engage the lead screw. The illustrated examples show slots 345, 346, 347, 348 in the nut housing portions 325, 326 that are arranged parallel to the lead screw axis, but other oblique configurations are possible.

As shown in FIG. 3F, the split nut 350 can be formed from nut portion 340 and nut portion 341. The nut portions 340, 341 can be sized and shape so that mating surface fit together to form passage 353 extending into or through the split nut 350. In an example, a first lead screw interface portion 351 in first nut portion 340 can be sized and shaped to align with a second lead screw interface portion 352 in second nut portion 341 to form an engagement passage 353 through the split nut 350. The lead screw interface portions 351, 352 can, for example, be threaded portions which together form a threaded passage. Other engagement portion configurations are possible, such a rack and pinion arrangement, a helical gear, or a belt drive system.

Referring again to FIG. 3F, nut portion 340 can include slots 345, 346. Nut portion 341 can include slots 347, 348. The slots 345, 346, 347, 348 can be sized and shaped to receive the pins 335, 336, 337, 338. In an example, slot 345 can be parallel to slot 346. The parallel alignment of slots 345, 346 can allow the nut portion 340 to slide on the pins without rotation of the nut portion. In the illustrated example, nut portion 340 can slide laterally away from nut portion 341 without moving proximally or distally relative to nut housing portion 325, and without rotating. The slots 347, 348 in nut portion 341 can also be parallel with each other. In the illustrated example, nut portion 341 can slide laterally away from nut portion 340 without nut portion 341 moving proximally or distally relative to nut housing portion 325, and without rotation of nut portion 341. Taken from another perspective, movement of the pins 335, 336 in a proximal direction can impose parallel forces on the nut portion 340 that bias the nut portion 340 laterally away from the lead screw axis, and movement of the pins 337, 338 in a proximal direction can impose parallel forces on nut portion 341 in a lateral direction away from the lead screw axis and away from nut portion 340. As will be further explained, proximal movement of the lever body can bias pins 335, 336, 337, 338 proximally, which causes the nut portions to slide laterally away from each other to the open position, which can disengage the nuts from the lead screw.

Portions of the slots 345, 346, 347, 348 in nut portions 340, 341, can be angled relative to the lead screw axis, so that movement of the pins biases the nut portions toward or away from the lead screw axis, depending on the direction of movement of the pins. In various examples, the slots can consist of a single line segment, the slots can each include a plurality of slot segments, and portions of the slots can be curved. In the Example illustrated in FIGS. 3A and 6, the slots each include two segments (better shown in FIG. 4.)

Figure 4A:
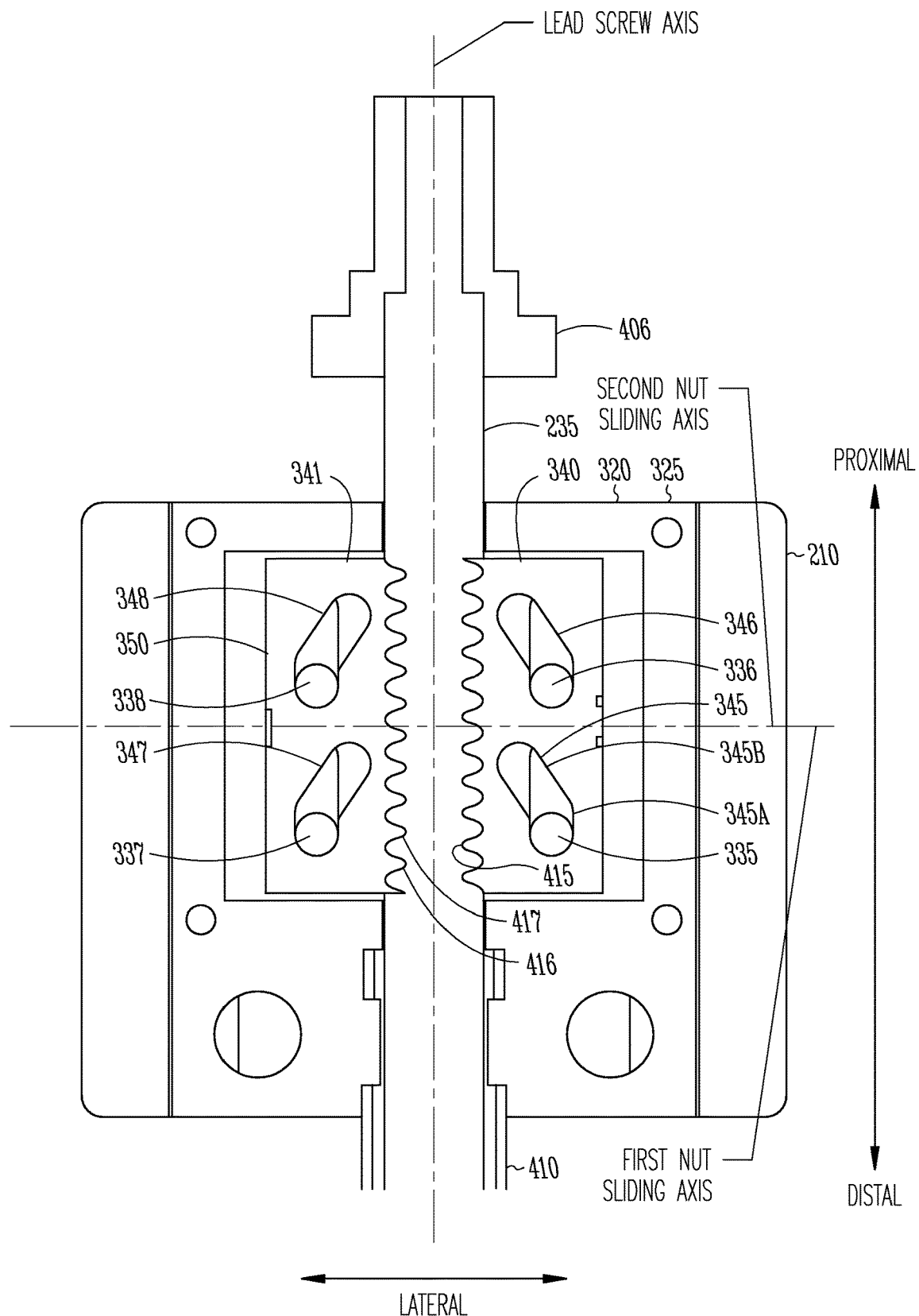
FIG. 4A is a cross-sectional view of the lever body, nut housing, and a nut taken along section A-A in FIG. 3B, additionally showing an example lead screw and a portion of a drive member.
Figure 4B:
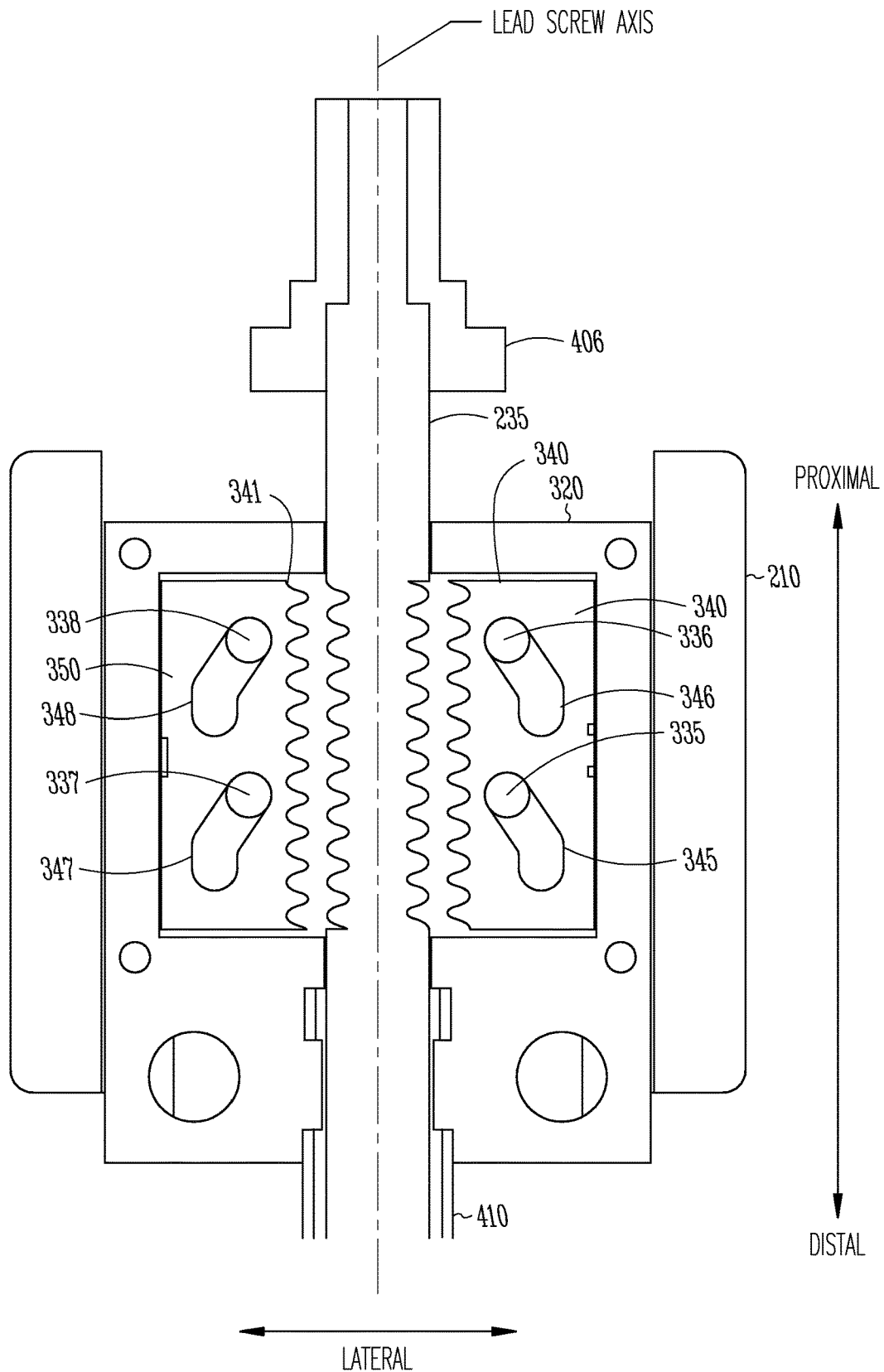
FIG. 4B is a cross-sectional view similar to FIG. 4A that shows the split nut in a disengaged position.

FIGS. 4A and 4B are cross-sectional views of the lever body 210, nut housing 320, and split nut 350 taken along section A-A in FIG. 3B, additionally showing an example lead screw 235 and a portion of an example drive member. While a drive tube 410 is shown in FIGS. 4A and 4B, other types of drive members are also possible. The lead screw can extend through the passage 330 in the nut housing 320 and through the passage 353 in the split nut. The lead screw can define a lead screw axis that can extend from a proximal end of the lead screw to a distal end of the lead screw and can run through the split nut coincident with a split nut axis. A coupling part 406 can be connected at or near the proximal end of the lead screw for connecting the lead screw to drive gear 240 (shown in FIG. 2B.) The lead screw can include an engagement portion 412, which can include threads, for example. Other engagement portion configurations are possible. For example, the engagement portion can include gear teeth (to engage with a rack, pinion, or helical gear), helical gear teeth, or surfaces sized and shaped to engage a belt.

FIG. 4A shows an example where the lead screw interfaces on the nut portions and the engagement portion on the lead screw include threads. The split nut 350 is shown in an engaged position, in which threads 415, 416 on the nut portions 340, 341 engage with threads 417 on the lead screw 235. The threads can be helical threads, or circumferential threads, for example. FIG. 4B shows the split nut in a disengaged position, in which threads 415, 416 on the nut portions 340, 341 are not engaged with threads 417 on the lead screw. In the disengaged position shown in FIG. 4B, the lead screw 235 can be movable along the lead screw axis relative to the nut housing 320. In an example, the split nut 350 can be disengaged from the lead screw by manually pulling up on the lever body, which causes the pins to move upward and causes the nut portions 340, 341 to move laterally away from the lead screw and out of engagement with the lead screw threads 417, at which point the lever body and drive tube can be moved in the proximal direction along the lead screw axis without turning the lead screw. This can allow, for example, withdrawal of a surgical tool coupled to a distal end of the drive tube from a surgical site.

As shown in FIG. 4A, nut portion 340 slides along first nut sliding axis, and second nut portion slides away from the lead screw axis along the second nut sliding axis. The first nut sliding axis can be parallel to the second nut sliding axis, both of which can be perpendicular to the lead screw axis, but other configurations are possible. For example, by manipulating the angle of the slots in the nut housing portions 325, 326 and nut portions 340, 341, the first nut sliding axis can be configured at an oblique angle to the lead screw axis. The angle between the first nut sliding axis can be the same, but is not necessarily the same, as the angle between the second nut sliding axis and the lead screw axis.

Various slot configurations are also possible. In the example illustrated in FIGS. 3A, 4A, and 4B, the slots include two segments (better shown in FIG. 4.) For example, slot 345 includes first segment 345A and second segment 345B. The other slots are similarly configured. The segments 345A, 345B can be sized and shaped to "lock" the nut portion into a closed position, so that a proximal force is required to disengage the nut portion 340 from the closed position and slide the nut portion 340 laterally away from nut portion 341.

Figure 5:
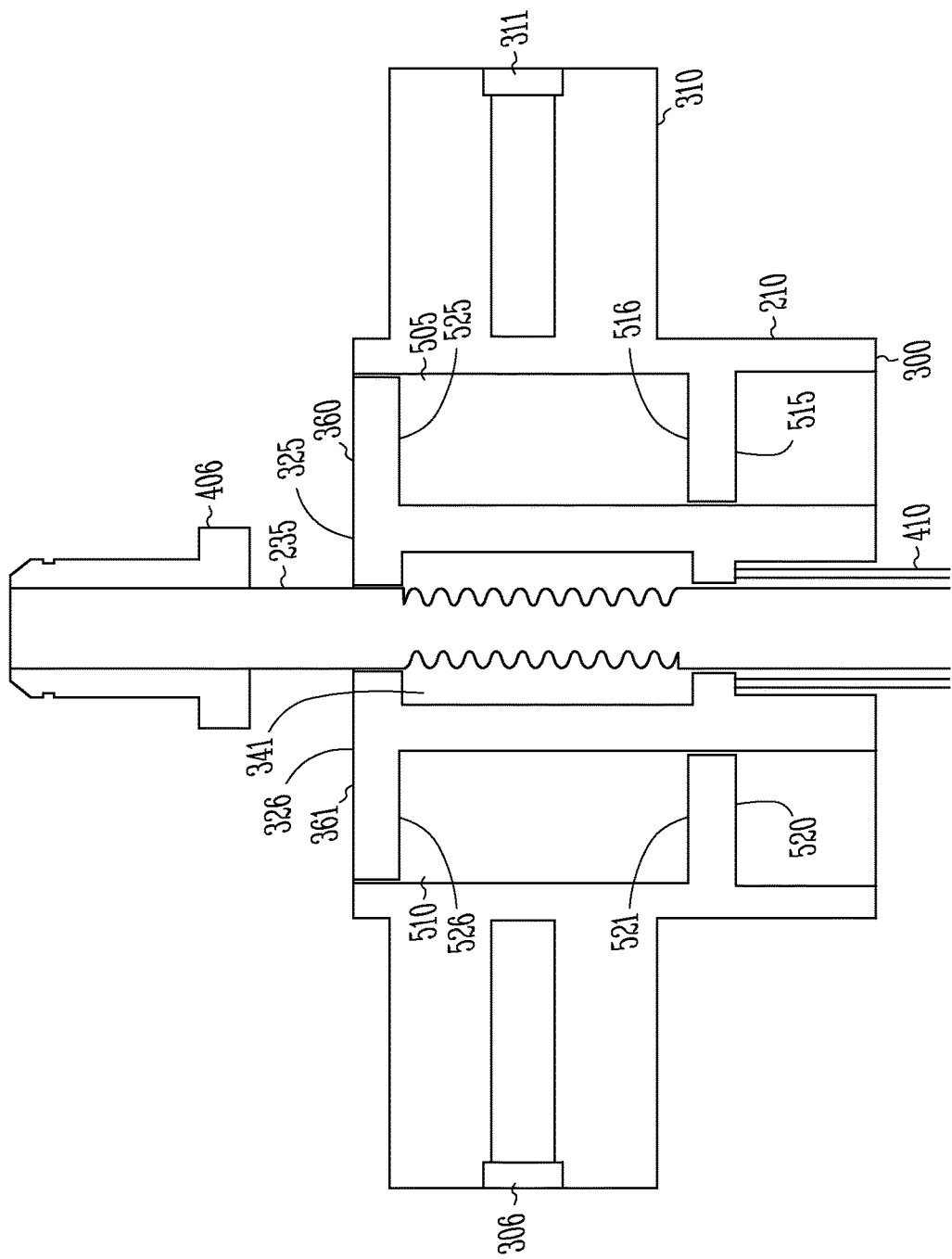
FIG. 5 is a cross-sectional view of lever body, nut housing, and nut taken along section B-B in FIG. 3B, additionally showing the example lead screw and a portion of a drive member.

FIG. 5 is a cross-sectional view of lever body 210, nut housing portions 325, 326, and nut portion 341 taken along section B-B in FIG. 3B, additionally showing lead screw 235 and a portion of a drive tube 410. Handles 215, 220 can be connected to holes 306, 311 using connection members (not shown) such as screws or press-fit connectors. Bias members 505, 510 can be situated in the interior cavity 315 of the main body 300 of the lever body 210. The bias members 505, 510 can, for example, be springs. The bias members 505, 510 can be situated against proximal faces 516, 521 of portions 515, 520 of the main body that extend into the interior cavity 315. The springs can be captured beneath distal faces 525, 526 on the extension portions 360, 361 of the nut housing portions 325, 326. In an example configuration, the springs can be configured to bias the nut housing portions 325, 326 to a position in which the split nut engages the lead screw 235. In this configuration, in a neutral state, the lead screw is engaged with the split nut 350, but the split nut 350 can be disengaged from the lead screw 235 by manual movement of the lever body 210.

Returning again to FIGS. 2A and 2B, in an example, in a first state, the lead screw interface on the nut is engaged with an engagement portion (e.g. threads) of the lead screw, rotation the drive gear 340 turns the lead screw and drives the nut and nut housing and connected components (e.g. lever body and handles) along the lead screw axis, and in a second state, the lead screw interface on the nut is not engaged with the engagement portion of the lead screw, turning the drive gear does not drive the nut and nut housing along the axis. In the second state, where the lead screw interface is not engaged with the engagement portion of the lead screw, the lever body, handles, and connected components (e.g. drive tube) can be manually retracted.

Figure 6:
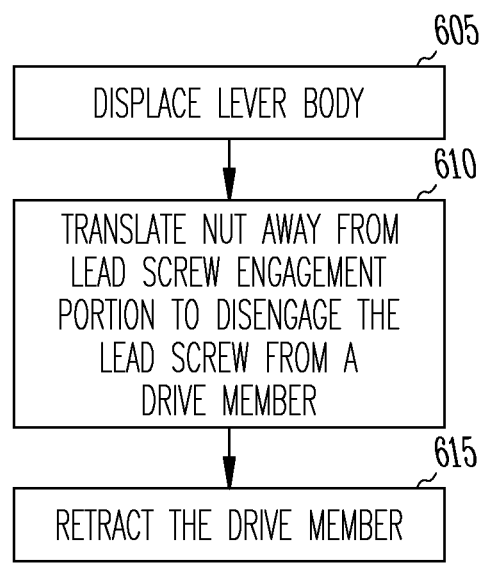
FIG. 6 is a flowchart illustrating a method of disengaging a lead screw from a drive member.

FIG. 6 is a flowchart illustrating a method of disengaging a lead screw from a drive tube. At 605, a lever body is displaced. In an example, the lever body can be manually displaced relative to a lead screw. For example, the lever body can be manually displaced along a lead screw axis. At 610, a nut is translated away from a lead screw engagement portion to disengage the lead screw from a drive member. In an example, the nut is translated when the lever body is displaced. In an example involving pins and a slots in a nut housing, displacing the lever body moves pins that extend through slots in a nut housing and a split nut. The pins convey forces to portions of the split nut to disengage the split nut from the lead screw. The split nut can be coupled to a nut housing that is coupled to the drive member. At 615, after the lead screw is disengaged, the drive member is retracted. In an example, a surgical tool is coupled to a distal end of the drive tube.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round", a component that is not precisely circular (e.g., one that is slightly oblong or is a many-sided polygon) is still encompassed by this description.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A medical device drive system comprising:
    a lever body including portions defining a lever body cavity;
    a lead screw extending through the lever body cavity, the lead screw having a proximal end, a distal end, and an engagement portion between the proximal end and the distal end, the proximal end and distal end defining a lead screw axis extending from the proximal end to the distal end;
    a first nut housing having a first nut cavity; the first nut housing being at least partially in the lever body cavity and being slidable in the lever body cavity along the lead screw axis;
    a first nut at least partially in the first nut cavity, the first nut having a first slot, and a lead screw interface sized and shaped to engage with the engagement portion of the lead screw, the first nut being slidable in the first nut cavity between an engaged position in which the lead screw interface is engaged with the engagement portion of the lead screw, and a disengaged position in which the lead screw interface is not engaged with the engagement portion of the lead screw; and
    a pin coupled to the lever body, the pin being slidable in the first slot of the first nut;
    wherein the lead screw interface of the first nut is selectively engageable with the engagement portion of the lead screw by sliding the lever body and the pin relative to the first nut housing along the lead screw axis.

2. The medical device drive system of claim 1, wherein the medical device drive system has a first state and a second state;
    in the first state the pin is in a first pin position in the first slot, the first nut housing is in a first nut housing position relative to the lever body, and the lead screw interface of the first nut is engaged with the engagement portion of the lead screw to prevent movement of the lead screw along the lead screw axis; and
    in the second state the pin is in a second pin position in the first slot, the first nut housing is in a second nut housing position relative to the lever body, and the lead screw interface of the first nut is not engaged with the engagement portion of the lead screw, the pin being slidable in the first slot from the first pin position to the second pin position as the first nut housing is moved from the first nut housing position to the second nut housing position.

3. The medical device drive system of claim 2, further comprising a spring in the lever body cavity, the spring sized and shaped to exert a biasing force on the first nut housing and the lever body, the biasing force biasing the pin toward the first pin position in the first slot of the first nut.

4. The medical device drive system of claim 1, further comprising:
   a second nut housing having a second nut cavity;
   a second nut having a second slot and a second lead screw interface sized and shaped to engage with the engagement portion of the lead screw, the second nut being at least partially in the second nut cavity and being slidable in the second nut cavity;
   a second pin coupled to the lever body, the second pin being slidable in the second slot of the second nut.

5. The medical device drive system of claim 4, wherein the first nut further includes a third slot, and the second nut further includes a fourth slot, and further comprising:
   a third pin coupled to the lever body, the third pin being slidable in the third slot; and
   a fourth pin coupled to the lever body, the fourth pin being slidable in the fourth slot.

6. The medical device drive system of claim 5, wherein the first slot defines a first pin path, the second slot defines a second pin path, the third slot defines a third pin path, and the fourth slot defines a fourth pin path, the third pin path being parallel to the first pin path, and the fourth pin path being parallel to the second pin path.

7. The medical device drive system of claim 4, wherein the first nut is slidable along a first nut sliding axis, the first nut sliding axis and the lead screw axis define a first angle; and the second nut is slidable along a second nut sliding axis, the second nut sliding axis and the lead screw axis define a second angle, the magnitude of the second angle being the same as the magnitude of the first angle.

8. The medical device drive system of claim 7, wherein the first nut sliding axis and second nut sliding axis are perpendicular to the lead screw axis.

9. The medical device drive system of claim 4, wherein:
   when the lever body is biased in a first direction along the lead screw axis, the first nut and second nut are biased away from the lead screw by the respective first pin and second pin; and,
   when the lever body is biased in a second direction along the lead screw axis, the first nut and second nut are biased toward the lead screw by the respective first pin and second pin.

10. The medical device drive system of claim 4, wherein the first nut is partially in the first nut cavity and partially in the second nut cavity, and the second nut is partially in the first nut cavity and the second nut cavity.

11. The medical device drive system of claim 1, further comprising:
    a chassis, the lead screw being rotatably coupled to the chassis, and the lever body being slidably coupled to the chassis; and
    a drive gear coupled to the lead screw and the chassis;
    wherein rotation of the drive gear turns the lead screw and drives the first nut and first nut housing along the lead screw axis when the lead screw interface on the first nut is engaged with the engagement portion of the lead screw.

12. The medical device drive system of claim 11, further comprising:
    a drive member coupled to the first nut housing, the drive member having a proximal end, and distal end, and a drive member axis defined by the proximal end and the distal end; and
    wherein rotation of the drive gear drives the drive member along the drive member axis.

13. The medical device drive system of claim 12, further comprising a surgical instrument coupled to the drive member and the lead screw, wherein rotation of the lead screw causes a first manipulation of the surgical instrument, and driving the drive member along the drive member axis causes a second manipulation of the surgical instrument.

14. A medical device comprising:
    a lead screw having a proximal end, a distal end, and a lead screw engagement portion between the proximal end and the distal end, the proximal end and distal end defining a lead screw axis extending from the proximal end to the distal end;
    a lever body, wherein the lever body includes portions defining a lever body cavity having a proximal end, a distal end, and a lever body axis defined between the proximal end and the distal end;
    a first nut having a first nut engagement portion sized and shaped to engage with the lead screw engagement portion, the first nut being slidably coupled to the lever body;
    a second nut having a second nut engagement portion sized and shaped to engage with the lead screw engagement portion, the second nut being slidably coupled to the lever body,
    the first nut and second nut being slidable toward and away from the lead screw axis; and;
    one or more drive portions coupled to the lever body, the one or more drive portions having one or more drive surfaces in contact with the first nut and the second nut, the one or more drive surfaces being oblique to the lead screw axis, wherein displacement of the lever body along the lead screw axis in a first direction biases the first nut and second nut toward the lead screw axis, and displacement of the lever body along the lead screw axis in a second direction biases the first nut and second nut away from the lead screw axis; and
    one or more nut housings having one or more nut body cavities, the one or more nut housings being at least partially in the lever body cavity and being slidable in the lever body cavity along the lever body axis, the first nut and the second nut each being at least partially in the one or more nut body cavities and being slideable in the one or more nut body cavities.

15. The medical device of claim 14, wherein the first nut includes a first slot, the second nut includes a second slot, and the one or more drive portions include one or more pins extending into the first slot and second slot.

16. The medical device of claim 14, wherein the one or more nut housings include:
    a first nut housing having portions defining a first nut cavity, the first nut being at least partially in the first nut cavity, and being slidable in the first nut cavity toward and away from the lead screw axis; and
    a second nut housing having portions defining a second nut cavity, the second nut being at least partially in the second nut cavity, and being slidable in the second nut cavity toward and away from the lead screw axis.

17. The medical device of claim 16, further comprising a drive member coupled to the one or more nut housings, an instrument coupled to a distal end of the drive member, and a drive system coupled to the lead screw and configured to turn the lead screw, wherein, when the first nut engagement portion is engaged with the lead screw engagement portion, turning the lead screw drives the first nut, the second nut, the first nut housing, the second nut housing, the drive member, and the instrument axially along the lead screw axis.

18. A selectively engageable medical device drive assembly comprising:
- a lever body having a proximal end, a distal end, and portions defining an interior cavity;
- a nut housing in the interior cavity of the lever body, the nut housing being slidable relative to the lever body, the nut housing having a proximal opening, a distal opening, portions defining a nut cavity, and portions defining a first nut housing slot and a second nut housing slot;
- a lead screw having a proximal end, a distal end, and a lead screw body extending from the proximal end to the distal end, the lead screw body defining a lead screw axis, the lead screw body extending through the proximal opening and distal opening in the nut housing, and an engagement portion of the lead screw being at least partially in the interior cavity of the nut housing;
- a split nut in the nut cavity, the split nut including a first nut part and a second nut part, the first nut part including a first engagement portion and a first nut slot, and the second nut part including a second engagement portion and a second nut slot; the first engagement portion and second engagement portion being sized and shaped to engage with the engagement portion of the lead screw; and
- a first pin in the first nut slot and the first nut housing slot, and a second pin in the second nut slot and the second nut housing slot.

19. The selectively engageable medical device drive assembly of claim 18, wherein sliding the nut housing relative to the lever body moves the first pin in the first nut slot and first nut housing slot, and moves the second pin in the second nut slot and second nut housing slot, the first pin and second pin biasing the first engagement portion of the first nut part and the second engagement portion of the second nut part out of engagement with the engagement portion of the lead screw.

\* \* \* \* \*

UNITED STATES PATENT AND TRADEMARK OFFICE
CERTIFICATE OF CORRECTION

PATENT NO. : 10,591,032 B2
APPLICATION NO. : 15/699441
DATED : March 17, 2020
INVENTOR(S) : Matthew A. Wixey Page 1 of 1

It is certified that error appears in the above-identified patent and that said Letters Patent is hereby corrected as shown below:

In the Claims

In Column 12, Line 35, in Claim 1, after "cavity;", insert --¶--

In Column 13, Line 37, in Claim 7, after "and", insert --¶--

In Column 13, Line 48, in Claim 9, delete "and," and insert --and-- therefor

In Column 14, Line 34, in Claim 14, after "axis;", delete "and;"

Signed and Sealed this
Second Day of June, 2020

Andrei Iancu
*Director of the United States Patent and Trademark Office*